United States Patent
Zhang et al.

(10) Patent No.: US 7,320,293 B2
(45) Date of Patent: Jan. 22, 2008

(54) **METHOD FOR CULTIVATING NOVEL SPECIES OF *HALIOTIS DISCUS HANNAI* INO WITH TANGERINE COLOR SHELL**

(75) Inventors: Guofan Zhang, Sandong (CN); Hongen Zhao, Sandong (CN); Xiao Liu, Sandong (CN)

(73) Assignee: Institute of Oceanology Chinese Academy of Sciences, Shenyang (CN)

( * ) Notice: Subject to any disclaimer, the term of this patent is extended or adjusted under 35 U.S.C. 154(b) by 204 days.

(21) Appl. No.: 10/532,675

(22) PCT Filed: Jul. 7, 2003

(86) PCT No.: PCT/CN03/00535
§ 371 (c)(1),
(2), (4) Date: Apr. 26, 2005

(87) PCT Pub. No.: WO2004/039150
PCT Pub. Date: May 13, 2004

(65) Prior Publication Data
US 2006/0162668 A1    Jul. 27, 2006

(30) Foreign Application Priority Data
Nov. 1, 2002  (CN) ............................... 02 1 44515

(51) Int. Cl.
*A01K 61/00* (2006.01)
(52) U.S. Cl. .................... 119/234; 119/236
(58) Field of Classification Search ............... 119/234, 119/236, 237, 239–241
See application file for complete search history.

(56) References Cited

U.S. PATENT DOCUMENTS

| | | | | |
|---|---|---|---|---|
| 4,183,322 A | * | 1/1980 | Shultz et al. | 119/236 |
| 4,226,210 A | * | 10/1980 | Lockwood et al. | 119/236 |
| 5,377,624 A | * | 1/1995 | Craig et al. | 119/234 |
| 5,758,602 A | * | 6/1998 | Fuglsang | 119/223 |
| 6,986,323 B2 | * | 1/2006 | Ayers | 119/200 |

FOREIGN PATENT DOCUMENTS

| | | | |
|---|---|---|---|
| CN | 1736344 A | * | 2/2006 |
| CN | 1739465 A | * | 3/2006 |
| JP | 2000245285 A | * | 9/2000 |
| JP | 2005261414 A | * | 9/2005 |

OTHER PUBLICATIONS

Shen, Jue-Fen, et al. "*Commercial seedling rearing of abalone Haiotis discus hannai in southern Shandong,*" Marine Sciences, (1996) No. 1, pp. 6-7.
Liu, Cong-De, "*Techniques for industrialization of seed breeding of abalone Haitos discuss hannai,*" Aquaculture, (1999) No. 1, pp. 3-4.
Zhong, You-Ping, et al., "*Techniques for industrialization of cultivation and seed breeding of abalone alone the southern coast of China,*" Journal of Jimei University (National Science), (1999) vol. 4, No. 1, pp. 51-52.

* cited by examiner

*Primary Examiner*—Yvonne R. Abbott
(74) *Attorney, Agent, or Firm*—Smith, Gambrell & Russell, LLP

(57) ABSTRACT

The invention refers to a method for breeding of a variety of Pacific abalone with orange shell. A new strain with uniform shell color of Pacific abalone is established by single mating or mass mating. The detailed procedures are as follows. The mature individuals with orange shell color are selected as breeders, and conditioned in the seawater. Macroalgae are fed and gentle aeration is provided daily. The gonad of breeders will eventually reach full ripeness; Artificial induction to spawn is conducted by combined desiccation, thermal shock and exposure to UV-irradiated seawater; The released gametes were fertilized by single mating or mass mating; A routine procedure is used for fertilized eggs incubation, larval and spat rearing. A new Pacific abalone strain of uniformly orange shell color is produced. In the invention, the new strain is produced by shell color mutant type abalone from natural populations or artificially cultivated stocks. No foreign genes are introduced. The methods are simple and feasible. The new strain has production traits superior to the common Pacific abalone. It is possible of the new abalone strain to bring about industrialization.

19 Claims, No Drawings

METHOD FOR CULTIVATING NOVEL SPECIES OF *HALIOTIS DISCUS HANNAI* INO WITH TANGERINE COLOR SHELL

FIELD OF THE INVENTION

The present invention relates a method for breeding of a variety of Pacific abalone with orange shell.

BACKGROUND OF THE INVENTION

Pacific abalone, *Haliotis discus hannai* Ino, is one of the most economically important species in Haliotdea family in China. It is naturally distributed along the coast of Japan, Korean Peninsula, and parts of the seaside of Liaoning and Shandong province in China. Pacific abalone is dominantly dioecious with external fertilization, and sexes are easily distinguished as an individual approaches sexual maturity: ovaries are dark blue and testes cream to white. Natural spawning occurs during July to August every year in Yellow and Bo Sea. The coasts of Dalian in Liaoning and Yantai, Weihai, Qingdao in Shandong are the main distribution in China. Pacific abalone is sorted to the species of moderate size in Haliotidea; however, it has the largest size among the members of Haliotdea distributed in China. Based on the tender meat textures and delicate favor, Pacific abalone has the best quality, highest price and most favorable popularity in China, which is generally called soft gold, and ranked the lead of Eight Precious Seafood. Pacific abalone is the exclusively commercial farming species in Yellow and Bo Sea in our country.

According to the depiction of Aquaculture Ministry of P. R. China on Pacific abalone, the wild type shell color is greenish brown or dark brown, generally called wild type color; while the shell color of the cultivated stocks is green, simply called wild cultivated type color. However, distinguished from the two types color abalone described above, another type color abalone with orange shell color is observed along the coast in northern China. Orange shell color individuals are the mutant type in Pacific abalone. The orange shell color abalone amounts only to less than 0.01% of the total stocks. With the exception of shell color, no differences in other major qualitative traits from common abalone are found. It is inferred the feasibility to develop a new abalone strain with identical orange shell color through systematic cross and selective breeding.

Comparison between common abalone and orange shell color ones shows that the latter has brighter shell color, and furthermore, higher disease resistance. The bright shell color makes the abalone more popular and a higher price in the market, and will increase the market share; while the high disease resistance trait is advantageous to the reduction of disease occurrence in the culture of the abalone, and will increase economic benefits. Orange shell color abalone performs a significant superiority in the traits of economic importance. Therefore, the orange shell color abalone has great commercial value.

Theories and experiments in genetic breeding demonstrate that hybridization (or inbreeding) and selective breeding are important approaches to develop new breeds. Many new breeds in agriculture, husbandry and fisheries are established by such methods.

SUMMARY OF THE INVENTION

The present invention is to provide an approach for developing a new strain of Pacific abalone for the purpose of breeding of a variety of Pacific abalone with orange shell.

For the purpose above-mentioned, program of this invention is by single mating or mass cross mating among orange shell color abalone, which amount to less than 0.01% of the total, from natural populations or artificially cultivated stocks. The detailed procedures are as follows.

1) Broodstock Selection

The mature abalones with orange shell color are selected from natural populations or cultivated stocks. Careful attention must be paid to exclude the individuals with foreign shell colors.

2) Broodstock Conditioning

The individuals of moderate or large size are selected as breeders. The breeders are subjected into 16~20° C. seawater at a stocking density of 25~80 individuals per $m^3$. Macroalgae are given daily. The tank-whole water is exchanged and the gentle aeration is provided every day. The light level is 20~100 Lux. When the effective cumulated temperature gets to 900~1400° C.•days, the gonad of the breeders will reach ripeness.

3) Induction of Spawning

The fully mature breeders are artificially induced to spawn by combined desiccation, thermal shock and exposure to UV-irradiated seawater. The detailed operations are: with desiccation for 60~120 minutes at the temperature of 18~20° C. and the humidity of 50~90% in the hatching room, the breeders are separated strictly in terms of sexes, and then individually immersed in seawater in different containers. The seawater is treated with 300~1000 mwh/L Ultra-violet and elevated at the temperature of 22~23° C. The breeders eventually release gametes within 40~90 minutes after seawater exchange.

4) The produced eggs and sperms are artificial fertilized by single mating or mass mating respectively.

5) A routine procedure is used for embryonic, larval and spat rearing. A new Pacific abalone strain with uniform orange shell color is established.

Furthermore, in step 2) the game of the breeders reaches ripeness by natural conditioning.

In step 2), the natural macroalgae refers to *Laminaria joponica, Undaria pinnatifida* and *Ulva pertus* or the combination of them.

In step 3), breeders are immersed into different containers respectively in term of sexes. The water volume of the containers depends on how many breeders it contains. Commonly, water volume of one breeder in the container is of a volume of 10~20 L.

In step 3), no gamete or insufficient gametes release may occur after immersing the breeders into elevated and UV-treated seawater within 40~90 minutes. In such case, the procedure of immersing the breeders into seawater of 22~23° C., 300~1000 mwh/L UV-treated for 40~90 minutes should be conducted once or twice. After that, sufficient gametes will be produced.

In step 4), the single mating refers to the mating between a male and a female from the same stock (population) or different stocks (populations). Mass mating refers to mating among males and females at the same or similar proportion.

The present invention has the following advantages:

The new strain, characteristic as uniformly orange shell color, is established with parents from shell color mutant type Pacific abalone in the natural populations or cultivated stocks. No foreign genes are introduced. The methods are simple and feasible. The new strain is superior in the production traits comparison with the common Pacific abalone. It is possible of the new abalone strain to bring about industrialization.

DESCRIPTION OF THE INVENTION IN DETAIL

The approach for developing the new abalone strain with identical orange shell color is further exemplified in detail.

EXAMPLE 1

An orange shell color family was established by single mating.

1) Broodstock

A female (RW, 8.5 cm shell length) and a male (Rh, 9.8 cm shell length) with brightly orange shell color were found in Dalian sea of China.

2) Conditioning

Rw, Rh and wild type color and wild cultivated type color breeders were conditioned with a stocking density of 25 individuals per m$^3$ at 20° C. Macroalgae such as *Laminaria joponica*, *Undaria pinnatifida* and *Ulva pertusa* were given daily, at 30% total body weight of the breeders. The water was exchanged and the gentle aeration was provided every day. The light level was 20 Lux. When the effective cumulated temperature was approximately 900° C.•days, the breeders reached ripeness. The mature characteristics were as follows: the gonad was full and bright on the surface; there was a clear mark between hepatopancrease and gonad covering the surface of the conical appendage; the gonad color of female and male was dark green and milky white, respectively.

3) Inducing of Spawning

The full mature breeders were artificially induced to spawn. After desiccation for 60 minutes at the temperature of 20° C. and the humidity of 50% in the hatching room, the breeders were individually immersed in seawater in 20 L containers. The seawater was treated with 300 mwh/L Ultraviolet and elevated at the temperature of 22° C. The seawater was replaced after 60 minutes. The breeders released gametes within 90 minutes after seawater exchange.

4) Fertilization

The gamete were equally divided into several portions and fertilized with sperms of males or eggs of females. The mating strategies were listed in the Table 1.

5) A routine procedure was conducted for embryonic, larval and spat rearing.

Approximately 80 days after fertilization, the progeny number of RwRh family was 34, 500. Shell length ranged from 0.5 cm to 1.0 cm. The shell color of RwRh family was uniformly orange, while that of the other families was wild cultivated type color. The shell color of family progeny was listed in the Table 1.

TABLE 1

The traits of Pacific abalone families and their parents

| | | Origin | |
| --- | --- | --- | --- |
| | | China | Japan |
| Male | Name; shell color | Rh (♂), orange color | Jm (♂), wild type color |

| Female | | | Progeny | | |
| --- | --- | --- | --- | --- | --- |
| Origin | Name | Family | Shell color | Family | Shell color |
| China | Rw | RwRh | Orange color | RwJm | Wild cultivated type color |
| | C$_1$ (♀) | C$_1$Rh | Wild cultivated type color | / | / |
| Japan | J$_1$ (♀) | J$_1$Rh | Wild cultivated type color | / | / |
| | J$_2$ (♀) | J$_2$Rh | Wild cultivated type color | / | / |
| | J$_4$ (♀) | J$_4$Rh | Wild cultivated type color | / | / |
| | J$_5$ (♀) | J$_5$Rh | Wild cultivated type color | / | / |
| | J$_6$ (♀) | J$_6$Rh | Wild cultivated type color | / | / |
| | J$_7$ (♀) | J$_7$Rh | Wild cultivated type color | / | / |
| | R$_j$ (♀) | R$_j$Rh | Wild cultivated type color | / | / |

(♀) means female; (♂) means male; J stands for Japan; Jm means number M individual from Japan.

The result showed that single mating between orange shell color parents produced orange shell color progenies.

A new Pacific abalone strain uniform shell color was produced. The qualitative characteristic was orange shell color. The quantitative characteristic was that the strain had 0-30% higher survival and 0-15% faster growth rate at the early stage than the common Pacific abalone.

EXAMPLE 2

The difference from example 1 was that an orange shell color stock was established by mass mating. The detailed operations were the following. In the step 2): the seawater for breeder conditioning was 16° C. The stock density was 80 individuals per m$^3$. The light level was 100 Lux. The effective cumulated temperature was approximately 1400° C.•days. In the step 3): the breeders were induced to spawn at a temperature of 20° C. and a humidity of 90% in the hatching room. After desiccation for 120 minutes, they were individually exposed to UV-treated seawater (1000 mwh/L). The seawater was elevated at the temperature of 23° C. The breeders released gametes within 40 minutes.

Broodstock: The breeders were selected from a cultivated stock in China and a wild population in Japan. The abalone with darkly orange shell color and brightly orange silky rings on the surface of the shell were selected from the stock, which was produced by inducing spawning and grew out indoors. The shell length range was 8.5-9.5 cm.

Mating strategies: A mass mating design was performed in the example. The P-RR stock (RwRh) was produced by eggs of 15 females mating sperms of 4 males. The gametes were equally pooled within each sex and stock. The eggs were artificially fertilized the sperms.

The routine procedure was used for fertilized eggs incubation and post-larvae rearing.

The orange shell color stock was produced by mass mating among orange shell color parents.

Approximately 100 days after fertilization, the progeny number of P-RR stock was 148,500. The shell length range was 0.6-0.9 cm. The shell color of P-RR stock was uniformly orange, while that of the other two stocks was wild cultivated type color. Information about the three stocks was listed in the Table 2.

TABLE 2

Shell color and index of the three stocks

|  | Stock | | |
| --- | --- | --- | --- |
|  | P-RR | P-JR | P-RJ |
| Origin and shell color | ♀: orange, China | ♀: Wild type color, Japan | ♀: orange, China |
|  | ♂: orange, China | ♂: orange, China | ♂: Wild type color, Japan |
| Eggs | 2,730,000 | 2,830,000 | 2,453,000 |
| Hatching rate (%) | 34 | 48 | 32 |
| Larvae transferred to a raceway | 921,600 | 1,357,200 | 784,800 |
| Raceway number | 3 | 4 | 2 |
| Settlement rate (%) | 19 | 17 | 20 |
| Spat after separation | 177,131 | 229,515 | 155,567 |
| Shell color of progeny | Orange | Wild cultivated type color | Wild cultivated type color |
| Spat on 24th August | 148,500 | 179,900 | 126,900 |
| Survival rate (%) | 84 | 78 | 82 |

EXAMPLE 3

A single mating design was performed to produce an orange shell color family.

The parent origin was the same as that in example 2, while the mating strategy was the same as that in the example 1. In the step 2): the seawater for breeder conditioning was 18° C. The stock density was 50 individuals per m$^3$. The light level was 50 Lux. The effective cumulated temperature was 1200° C.•days. In the step 3): the breeders were induced to spawn at a temperature of 18° C. and at a humidity of 70% in the hatching room. After desiccation for 90 minutes, they were individually exposed to UV-treated seawater (700 mwh/L). The seawater was elevated at the temperature of 23° C. The breeders released gametes within 60 minutes. RR family was produced by shell color mutant type parents. The female and male were designated R-3 and R-4, respectively. The number of RR family was 37,800. The shell length range was 1.2-1.8 cm. The shell color of RR family was uniformly orange. Information about the three families was listed in the Table 3.

TABLE 3

Shell color and index of the three families

|  | Families | | |
| --- | --- | --- | --- |
|  | RR | JR | RJ |
| Spawning time | 13th, May | 13th, May | 13th, May |
| Breeder characteristics | ♀: orange ♂: orange | ♀: Wild type color ♂: orange | ♀: orange ♂: Wild type color |
| Eggs | 230,000 | 195,000 | 145,000 |
| Hatching rate (%) | 44 | 42 | 30 |

TABLE 3-continued

Shell color and index of the three families

|  | Families | | |
| --- | --- | --- | --- |
|  | RR | JR | RJ |
| Larvae transferred to a raceway | 100,800 | 82,800 | 43,200 |
| Settlement rate (%) | 39 | 2 | 40 |
| Separation time | 16th, July | 8th, August | 30th, July |
| Spat after separation | 39,497 | 1,632 | 17,342 |
| Shell color of progeny | Orange | Wild cultivated type color | Wild cultivated type color |
| Spat on 24th August | 37,758 | 1,560 | 16,999 |
| Survival rate (%) | 96 | 96 | 98 |

PJ stands for orange mutant R-3 as the maternal and wild individual from Japan as the paternal; JR stands for wild individual J-12 from Japan as the maternal and orange mutant R-4 as the paternal.

In a summary, the new Pacific abalone strain was produced by mating among orange shell color individuals. In another word, either of parents, whose shell color wasn't orange, wasn't used to produce the new strain. It was difficult to obtain orange shell color stocks by naturally spawning due to a rare abundance of orange shell color individuals and a mass of greenish brown (or dark brown) shell color (wild type color) or green shell color (wild cultivated type color) ones in the stocks. The invention is to solve how to produce the orange shell color strain with an aim to culture the strain in a large scale.

What is claimed is:

1. A method for breeding of a variety of Pacific abalone having an orange shell, which comprises
    selecting breeders having an orange shell color from a broodstock;
    conditioning the breeders to maturity;
    inducing the mature breeders to spawn;
    fertilizing the eggs released by the breeders; and
    rearing the progeny resulting from the fertilized eggs.

2. The method of claim 1, wherein the breeders are moderate to large in size.

3. The method of claim 1, wherein the broodstock excludes abalones lacking orange shell colors.

4. The method of claim 1, wherein the broodstock is selected from natural populations or cultivated stocks.

5. The method of claim 1, wherein the breeders are conditioned in seawater at about 16 to about 20° C. and a stocking density of about 28 to about 80 abalones per one cubic meter.

6. The method of claim 1, wherein the breeders are spontaneously conditioned.

7. The method of claim 1, wherein the broodstock is conditioned at a light level of about 20 to about 100 Lux.

8. The method of claim 1, wherein the eggs are fertilized by single matings or mass matings.

9. The method of claim of claim 8, wherein eggs of a plurality of female abalone are fertilized by sperm from a plurality of male abalone in the same or similar proportion.

10. The method of claim 1, wherein the eggs are artificially fertilized.

11. The method of claim 1, wherein the breeders are induced to spawn in a container.

12. The method of claim 1, wherein the breeders are induced to spawn by subjecting the breeders to desiccation, thermal shock and UV-irradiated seawater.

13. The method of claim 12, wherein the UV-irradiated seawater was treated with about 300 to about 1000 mwh/L UV light at a temperature of about 22 to about 23° C.

14. The method of claim 12, wherein desiccation occurs for about 60 to about 120 minutes at a temperature of about 18 to about 20° C. and a humidity of about 50 to about 90%.

15. The method of claim 12, further comprising repeatedly subjecting the breeders to desiccation, thermal shock and UV-irradiated seawater until sufficient gametes are released.

16. The method of claim 1, wherein macroalgae is added to the seawater and the seawater is aerated daily.

17. The method of claim 16, wherein the macroalgae is *Laminaria joponica, Undaria pinnaufida, Ulva pertus*, or a combination thereof.

18. The method of claim 1, wherein the breeders are conditioned in seawater at about 16 to about 20° C.

19. The method of claim 1, wherein the breeders are conditioned at a stocking density of about 28 to about 80 abolones per one cubic meter.

* * * * *